(12) United States Patent
Wood et al.

(10) Patent No.: US 6,866,667 B2
(45) Date of Patent: Mar. 15, 2005

(54) PATELLAR MILLING CLAMP

(75) Inventors: Steven R. Wood, Warsaw, IN (US); Bryan C Mendenhall, Claypool, IN (US); Paul E. Salyer, Warsaw, IN (US)

(73) Assignee: Symmetry Medical, Inc., Warsaw, IN (US)

(*) Notice: Subject to any disclaimer, the term of this patent is extended or adjusted under 35 U.S.C. 154(b) by 346 days.

(21) Appl. No.: 10/234,916

(22) Filed: Sep. 3, 2002

(65) Prior Publication Data

US 2004/0087961 A1 May 6, 2004

(51) Int. Cl.[7] ............................................. A61B 17/16
(52) U.S. Cl. .................................. 606/96; 606/86
(58) Field of Search .................... 606/79–80, 96–98, 606/87–88, 205–509

(56) References Cited

U.S. PATENT DOCUMENTS

| | | |
|---|---|---|
| 2,291,413 A | 9/1942 | Siebrandt |
| 2,427,128 A | 9/1947 | Ettinger |
| 2,698,483 A | 1/1955 | Berkowitz ...................... 32/63 |
| 3,037,405 A | 6/1962 | Steyskal ...................... 77/34.5 |
| 3,126,767 A | 3/1964 | Sawyer ........................ 77/33.4 |
| 3,724,963 A | 4/1973 | Stadtmiller .................. 408/14 |
| 3,979,165 A | 9/1976 | Pyle ............................. 408/14 |
| 4,312,337 A | 1/1982 | Donohue |
| D273,326 S | 4/1984 | Peterson et al. ............. D24/27 |
| 4,444,180 A | 4/1984 | Schneider et al. |
| 4,565,192 A | 1/1986 | Shapiro |
| 4,586,497 A | 5/1986 | Dapra et al. |
| 4,633,862 A | 1/1987 | Petersen |
| 4,706,660 A | 11/1987 | Petersen |
| 4,736,737 A | 4/1988 | Fargie et al. |
| 4,750,481 A | 6/1988 | Reese |
| 4,952,213 A | 8/1990 | Bowman et al. ............... 606/79 |
| 5,002,547 A | 3/1991 | Poggie et al. .................. 606/88 |
| 5,021,055 A | 6/1991 | Burkinshaw et al. ......... 606/82 |
| 5,129,907 A | 7/1992 | Heldreth et al. ............... 606/80 |
| 5,486,177 A * | 1/1996 | Mumme et al. ............... 606/79 |
| 5,536,271 A * | 7/1996 | Daly et al. ..................... 606/80 |
| 5,716,360 A * | 2/1998 | Baldwin et al. ............... 606/80 |
| 6,277,121 B1 * | 8/2001 | Burkinshaw et al. ......... 606/80 |

OTHER PUBLICATIONS

Richards Tricon Total Knee System–Tricon–M With Pro–Fit Surgical Procedures–4 pages including pp. 14–15.
Richards–Genesis Total Knee System: Addressing the Unexpected–Cruciate–Retaining Primary Technique–pp. 21–23, 34.
Biomet Inc. AGC–Total Knee System: Patellar Instrumentation 1990.
Depuy–AMK Total Knee System Design Rationale and Surgical Procedure–Engh et al.–3 pages including p25.
Dow Corning Wright–Whiteside ORTHOLOC II Total Knee System: Surgical Technique Patella Recessing–pp. 1–5.
Dow Corning Wright–"We—re Pushing All the Wright Buttons."
Intermedics Orthopedics, Inc.–The Intermedics Natural–Knee System–Hoffman–pp. 23–24.
Richards–pp. 37–38–Various Patellar Instruments.

* cited by examiner

*Primary Examiner*—David O. Reip
*Assistant Examiner*—D. Jacob Davis
(74) *Attorney, Agent, or Firm*—Taylor & Aust, P.C.

(57) ABSTRACT

A patellar milling clamp is provided with a depth control for limiting and controlling the milling depth of a grater rotated against a bone secured in the milling clamp. A stop ring is provided on a shaft of the milling tool. The shaft is slidable in a guide bushing of the milling clamp, and a rotatable cap on the guide bushing is selectively engaged in notches in the guide bushing to provide an abutment surface at selectively different elevations. Further advancement of the tool is prevented when the stop ring abuts the abutment surface of the cap. The depth of milling is precisely controlled regardless of the original thickness of the patellar bone being milled.

21 Claims, 5 Drawing Sheets

PATELLAR MILLING CLAMP

BACKGROUND OF THE INVENTION

1. Field of the Invention

The present invention relates generally to surgical instruments, and more particularly to a patellar milling clamp and adjustable stops used with patellar milling clamps.

2. Description of the Related Art

A patellar implant is applied to a prepared patella either by surface attachment, referred to as an onlay procedure, or by recessing the implant into the patella, referred to as an insetting procedure. In an onlay procedure, the posterior patella surface is milled flat, to provide a suitable surface for attachment of the implant. In an insetting procedure, the posterior patella surface is milled to provide a cavity for receiving the implant, with a rim of bone remaining around the periphery of the implant. In either procedure, the patella must be secured firmly, relative to the milling tools used, and the milling tools must be guided accurately against the patella as the milling procedure progresses.

Various types of clamps and holders have been used for securing a patella when performing milling procedures. It is known to provide tool guides associated with the clamps, so that the tool is guided accurately towards the patella. A clamp must be capable of securing patellae of different sizes, and the tool guide must be adaptable for use with different size graters required for different size implants.

It is desirable to provide a milling tool guide including a stop, so that continued advancement of the milling tool, and continued milling of the patella is prevented after a predetermined amount of surface milling has occurred. Tool stops generally are known, and have included apparatus to prevent further advancement of the milling tool dependent upon the amount of material remaining in the patella. For example, U.S. Pat. No. 5,129,907 "PATELLAR CLAMP AND REAMER WITH ADJUSTABLE STOP" includes an adjustable stop calibrated with indicia for indicating the thickness of patellar bone remaining when the stop is engaged. In using such a device, the surgeon is required to calculate the amount of patellar bone material to be recessed to accept a patellar implant in an insetting procedure. The surgeon must also consider and calculate the amount such that sufficient patellar bone thickness remains after resection. With stops of this type, more bone thickness than necessary may be removed for insetting the implant or for preparing and smoothing the surface to receive an implant in an onlay procedure.

What is needed in the art is a patellar milling clamp that securely holds a patella while guiding a tool against the patella during a milling procedure, with an adjustable stop adjusted to remove only a sufficient amount of bone for the implant being used, regardless of the original patella bone thickness.

SUMMARY OF THE INVENTION

The present invention provides a patellar milling clamp having upper and lower jaws for clamping a bone therebetween, and a milling tool guide tower affixed to the upper jaw. The guide tower has an adjustable depth stop to terminate advancement of the tool after a predetermined amount of bone has been removed.

The invention comprises, in one form thereof, a patellar milling clamp for guiding a milling tool during a patella milling procedure. The milling tool has a shaft that is used for driving a milling grater. The clamp has a first jaw and a second jaw associatively connected to clamp a patella therebetween. A grater guide and a shaft guide are secured relative to the first jaw. The shaft guide has a top with a plurality of fixed elevations. A cap is adapted for engaging a selected one of the elevations to establish a variable height abutment surface. A stop is associated with the shaft for engaging the abutment surface and terminating movement of the shaft toward the second jaw.

In another form thereof, the invention comprises a surgical instrument for clamping a bone and guiding a milling tool against the bone. The instrument has an upper handle assembly and a lower handle assembly crossed with and pivotally connected to each other. An upper jaw assembly is connected to the lower handle assembly; a lower jaw assembly is connected to the upper handle assembly. A guide tower is detachabably affixed to the upper jaw assembly, and includes a guide bushing having a plurality of fixed elevations and a cap selectively positioned for engaging a selected one of the plurality of fixed elevations.

The invention comprises, in still another form thereof, a bone milling depth control for a surgical instrument having top and bottom jaws for clamping a bone, and a milling tool guide for positioning a milling tool relative to the bone during a milling procedure, the milling tool being driven by a shaft. The depth control includes a bushing spaced from and in alignment with the milling tool guide. The bushing is adapted for guiding the shaft for axial movement. The bushing has an end surface and a plurality of fixed elevations at different spaced distances from the end surface. A cap is slidable over the bushing for selectively engaging a selected one of the fixed elevations. A ring is fixed to the shaft for abutting the cap to restrict axial advancement of the shaft toward a bone clamped in the jaws.

An advantage of the present invention is providing a milling tool guide that securely clamps a bone during a milling procedure, and accurately guides a milling tool during the milling procedure.

Another advantage is providing a patellar milling clamp with an adjustable stop permitting removal of a fixed amount of bone during a milling procedure, regardless of original bone thickness.

Yet another advantage is providing a patellar milling clamp with an adjustable depth stop that is easy to adjust, accurate in adjustment, and firmly held in the adjusted position.

BRIEF DESCRIPTION OF THE DRAWINGS

The above-mentioned and other features and advantages of this invention, and the manner of attaining them, will become more apparent, and the invention will be better understood, by reference to the following description of an embodiment of the invention, taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
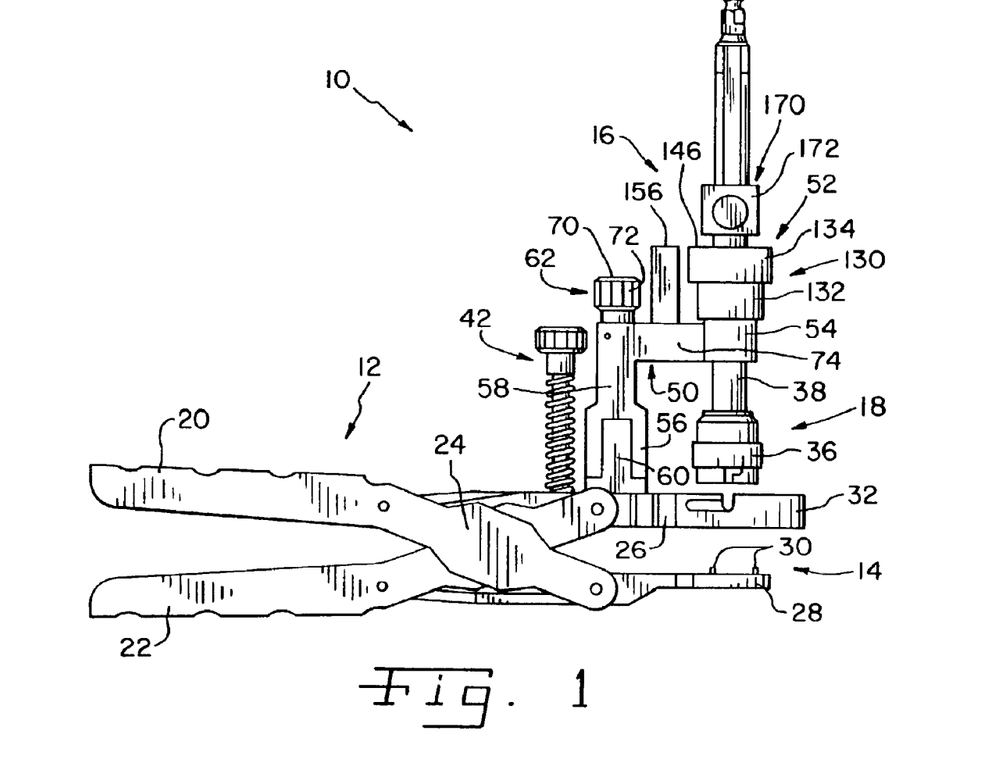
FIG. 1 is a side-elevational view of a patellar milling clamp according to the present invention.

Referring now to the drawings, and more particularly to FIG. 1, there is shown a surgical instrument in the form of patellar milling clamp 10 of the present invention. Milling clamp 10 generally includes a handle assembly 12, a clamping assembly 14 and a milling tool guide tower assembly 16. Milling clamp 10 operates in cooperation with a milling tool 18 during the performance of a milling procedure on a patella bone (not shown). Milling clamp 10 is constructed of surgical instrument quality materials, such that it may be cleaned and sterilized for repetitive use. It is readily disassembled, as will be described, so that it may be cleaned thoroughly between uses.

Handle assembly 12 includes an upper handle 20 and a lower handle 22 that are crossed with each other at an area 24 of crossed handles 20 and 22.

Clamping assembly 14 includes an upper jaw assembly 26 detachably connected to lower handle 22, and a lower jaw assembly 28 detachably connected to upper handle 20. Thus, handle assembly 12 and clamping assembly 14 have an appearance through connection area 24 to function similarly to that of pliers or scissors. A patella bone can be clamped between upper jaw assembly 26 and lower jaw assembly 28. To assist in clamping and secure fixation of a patella bone between upper jaw assembly 26 and lower jaw assembly 28, lower jaw assembly 28 may be provided with one or more prongs 30, to partially embed in the patella bone, and prevent the bone from sliding relative to clamping assembly 14. Also, distal portions of jaw assemblies 26 and 28 can be shaped advantageously to retain a patella bone between them.

Upper jaw assembly 26 includes a grater guide 32 detachably affixed thereto. Grater guide 32 is essentially a ring, or annular body, best seen in FIG. 2, sized to receive therein a grater (not shown) of milling tool 18. Grater guide 32 and the grater (not shown) are sized such that the grater will slide through grater guide 32, with minimal play such that the grater is precisely moved relative to a patellar bone affixed between upper jaw assembly 26 and lower jaw assembly 28.

The grater (not shown) is detachably affixed by a bayonet style coupling 36 on a drive shaft 38 of milling tool 18. Milling tool 18 further includes a pneumatic or other drive device (not shown) providing rotational power to shaft 38, for rotating the grater to perform a milling procedure against a patella bone.

Figure 2:
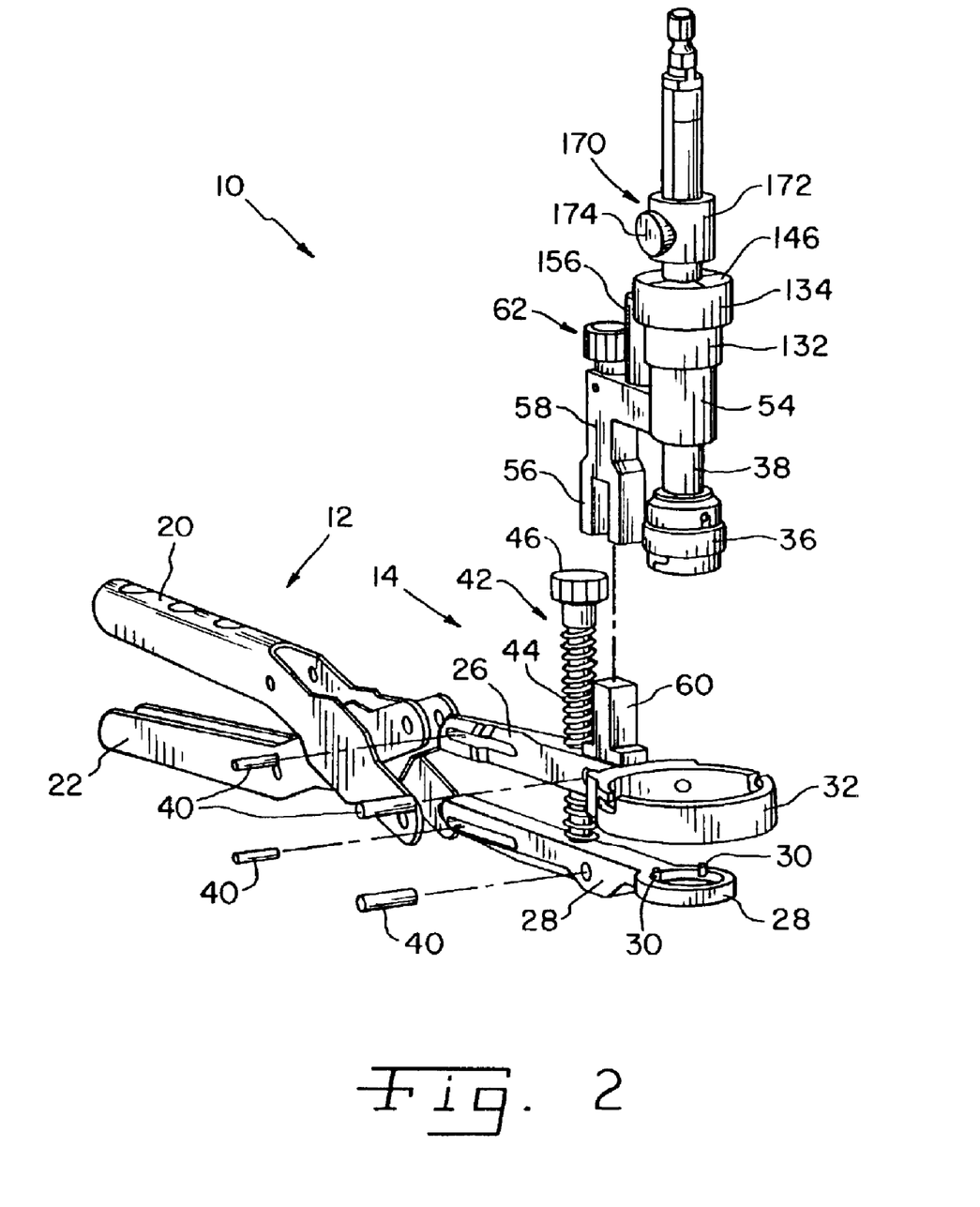
FIG. 2 is an exploded perspective view of the milling clamp shown in FIG. 1.

It should be understood that for different size patella bones and/or for different size implants, different size graters will be required, and different size grater guides 32 used for directing and positioning grater 34 relative to the patella bone. A plurality of pins 40 are used for securing upper jaw assembly 26 and lower jaw assembly 28 to lower handle 22 and upper handle 20, respectively, and for securing grater guide 32 in upper jaw assembly 26. Four such pins 40 are shown in FIG. 2.

Movement of jaw assemblies 26 and 28 toward or away from each other can be performed by rotation of a driver 42 having threads 44 engaged with and extending through upper jaw assembly 26. An outer end of driver 42 includes a knob 46 to assist a user of clamp 10 in grasping and turning driver 42. An inner end of driver 42 is rotatably secured to, but not threadedly engaged with lower jaw assembly 28. Thus, jaw assemblies 26 and 28 can be caused to move toward or away from each other by rotation of driver 42. Rotation of driver 42 in one direction causes upper jaw assembly 26 to climb along threads 44 toward knob 46, and rotation of driver 42 in the opposite direction causes upper jaw assembly 26 to descend on the threads toward lower jaw assembly 28. Further, when not being rotated, driver 42 holds jaw assemblies 26 and 28 in fixed spaced relation to each other.

Guide tower assembly 16 includes a guide tower 50 detachably secured to upper jaw assembly 26. An adjustable milling depth control 52 is operatively associated with and part of guide tower assembly 16, for limiting the extent to which shaft 38 can be advanced towards a bone secured in clamping assembly 14. Guide tower 50 has a guide for shaft 38 in the nature of a guide bushing 54 that is essentially a cylindrical tube of proper size to slidably receive shaft 38 therein. Guide bushing 54 is axially aligned with grater guide 32, for guiding milling tool 18 linearly, toward and away from a patella held in clamping assembly 14.

Guide tower 50 is detachably secured to upper jaw assembly 26 via a fork 56 extending downwardly from a leg 58 of guide tower 50. Fork 56 engages a post 60 extending upwardly from upper jaw assembly 26. A screw 62 extends through a hole 64 (FIG. 3) in leg 58, and includes threads 66 that engage threads in a hole (not shown) in post 60. Screw 62 further includes a head 70 having knurls or ridges 72 for grasping screw 62 such that screw 62 may be finger tightened in the hole 68, to detachably secure guide tower 50 on upper jaw assembly 26. Advantageously as shown, post 60 is square or rectangular in cross section, with at least two flat sides for engaging against flat sides of fork 56, to prevent rotation of fork 56 on post 60. Screw 62 need be tightened only sufficiently to seat fork 56 on post 60 snuggly, but need not be overly tightened. Cooperative structures other than fork 56 and post 60 can be used for accurately positioning tower 50 on upper jaw assembly 26, as those skilled in the art will understand readily.

Leg 58 is connected to guide bushing 54 by an arm portion 74 of guide tower 50. Preferably, guide bushing 54, arm 74, leg 58 and fork 56 are formed integrally as a monolithic body.

Depth control 52 is a cooperative assembly between structures of and on guide bushing 54 and structures on shaft 38. Guide bushing 54 includes a top end 90 and a bottom end 92. A plurality of notches 94, 96, 98 and 100 (FIGS. 6 through 10) are provided extending downwardly from top end 90 at the outer surface of guide bushing 54. As shown in the drawings, guide bushing 54 includes four notches 94, 96, 98 and 100, but also may include fewer than four notches, or more than four notches. Each notch 94, 96, 98 and 100 includes a floor 104, 106, 108 and 110, respectively. Each floor 104, 106, 108 and 110 is a preestablished different distance from top end 90, thereby providing a plurality of different fixed elevations on guide bushing 54. Each notch 94, 96, 98 and 100 further includes a flattened face 114, 116, 118 and 120, respectively, extending between floor 104, 106, 108 and 110, respectively, and top end 90.

Notches 94, 96, 98 and 100 are spaced from each other by lands 122, 124, 126 and 128. Notches 94 and 96 are adjacent each other, and separated by land 122. Notches 96 and 98 are adjacent each other, and separated by land 124. Notches 98 and 100 are adjacent each other, and separated by land 126. Notches 94 and 100 are adjacent each other, and separated by land 128. As shown, notches 94, 96, 98 and 100 are spaced evenly around guide bushing 54, but need not necessarily be evenly spaced.

Figure 3:
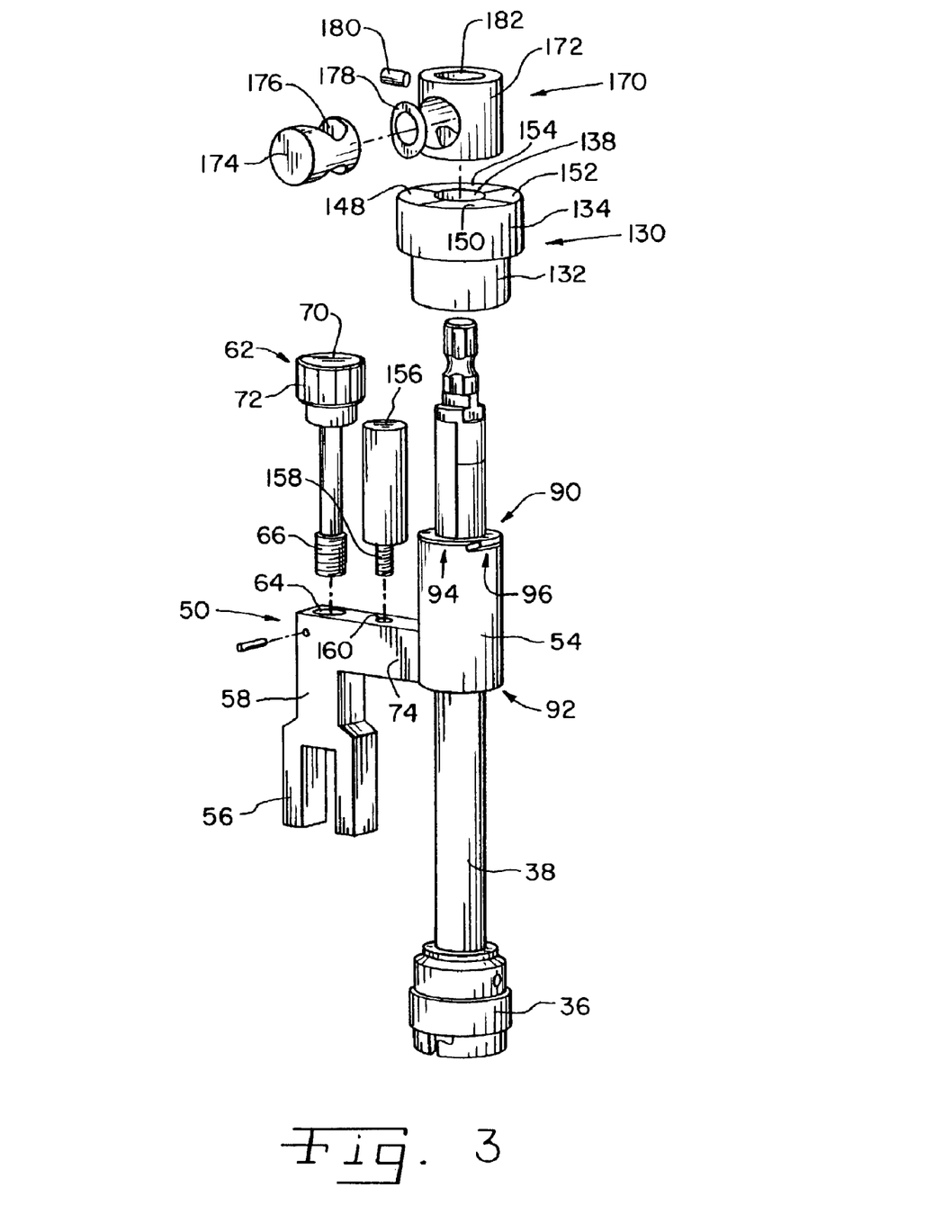
FIG. 3 is an exploded perspective view of the guide tower assembly portion of the milling clamp shown in the previous drawings.
Figure 4:
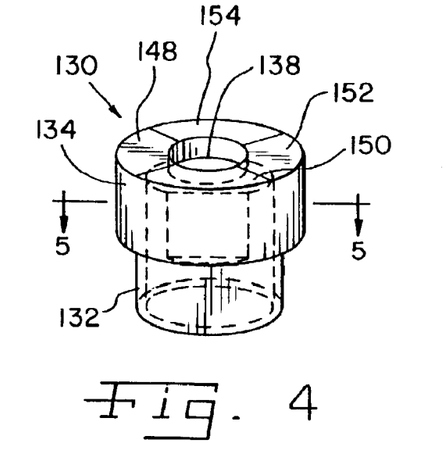
FIG. 4 is perspective view of the cap for the guide tower.
Figure 5:
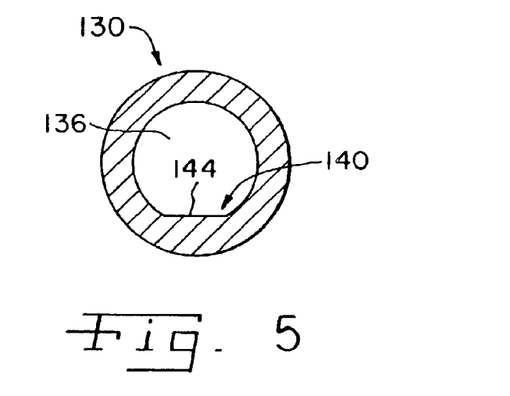
FIG. 5 is a cross-sectional view of the cap, taken along line 5—5 of FIG. 4.
Figure 6:
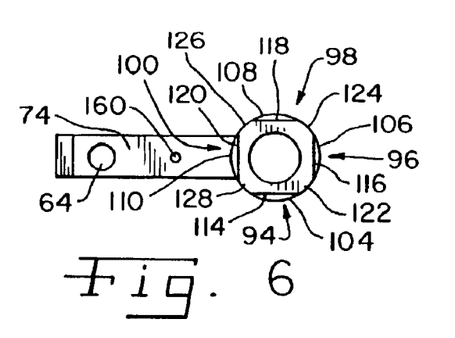
FIG. 6 is a top view of the guide tower.
Figure 7:
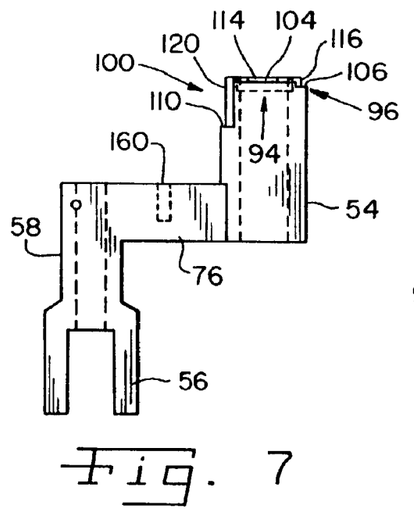
FIG. 7 is an elevational view of one side of the guide tower.
Figure 8:
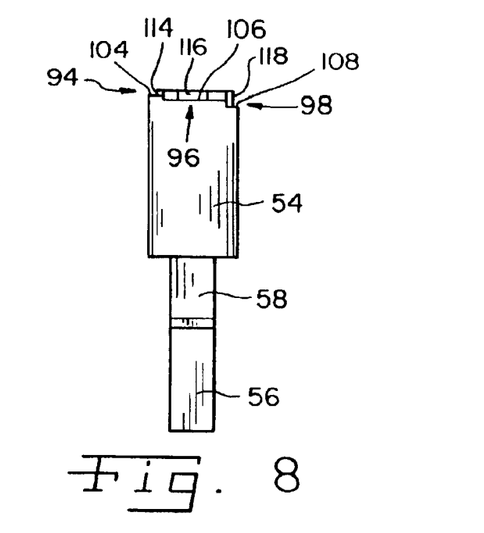
FIG. 8 is an elevational view of one end of the guide tower.
Figure 9:
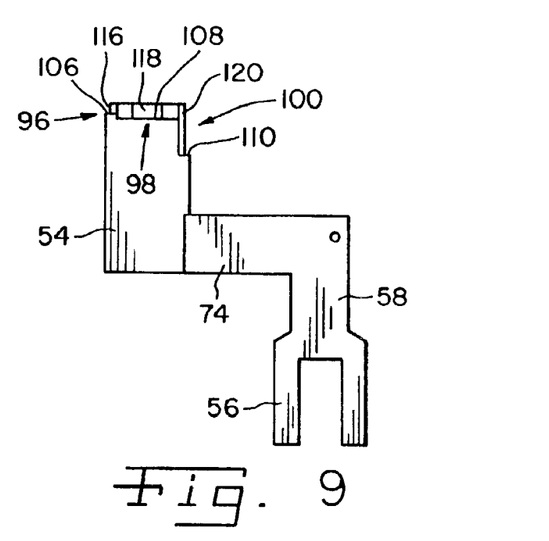
FIG. 9 is another side elevational view of the guide tower, showing the side opposite the side shown in FIG. 7.
Figure 10:
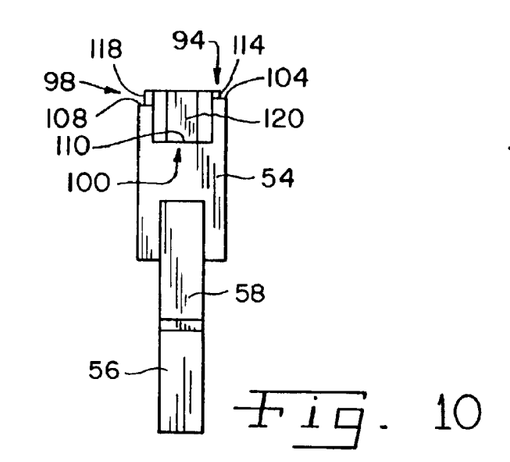
FIG. 10 is another end elevational view of the guide tower, showing the end opposite the end shown in FIG. 8.
Figure 11:
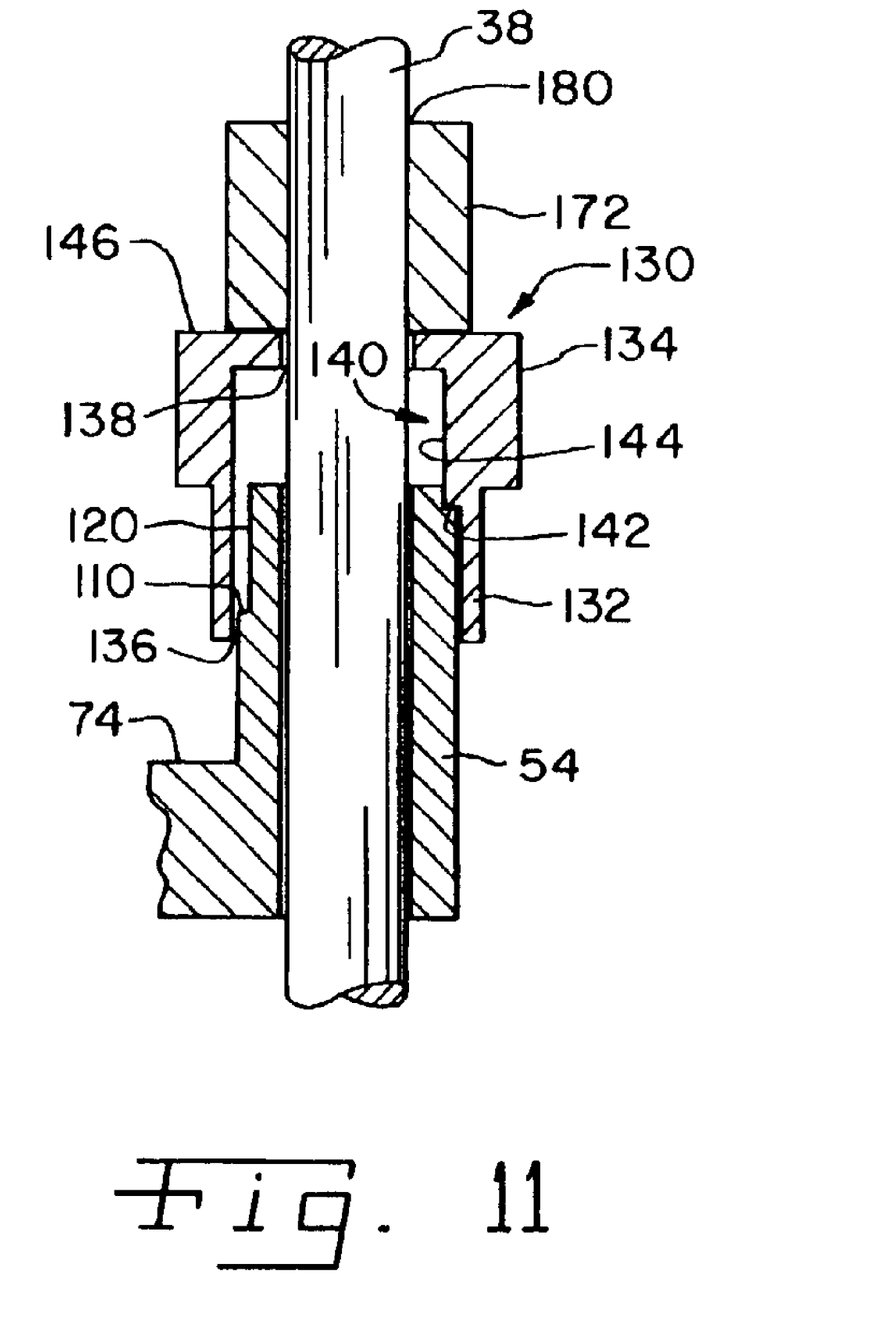
FIG. 11 is an enlarged cross-sectional view of the milling tool stop in accordance with the present invention.

Depth control 52 further includes a cap 130 having a cylindrical body 132 and a top 134 (FIGS. 4 and 5). An axial opening 136 through body 132 is sufficiently large to allow cap 130 to slide over top end 90 of guide bushing 54. Top 134 includes a narrowed opening 138 sufficient for cap 130 to slide over shaft 38, but not sufficiently large for top 134 to slide completely over guide bushing 54. Within axial opening 136, an indexing key 140 extends downwardly from top 134. Indexing key 140 has a width and depth to be received in any of notches 94, 96, 98 and 100. A bottom surface 142 (FIG. 11) of indexing key 140 rests on any of floors 104, 106, 108 and 110. The body of key 140, and particularly an inner wall 144 thereof, extends upwardly from bottom surface 142, along the respective face 114, 116, 118 or 120 of the notch 94, 96, 98 or 100 in which indexing key 140 is received. Thus, by rotating cap 130 on guide bushing 54, indexing key 140 can be positioned in any of the notches 94, 96, 98 and 100. By doing so, an abutment surface 146 on top 134 of cap 130 can be positioned at selective elevations with respect to guide bushing 54. Abutment surface 146 can be scribed or otherwise marked into quadrants 148, 150, 152 and 154 and provided with numerical markings indicating the milling depths when indexing key 140 is seated in a particular notch 94, 96, 98 or 100. A post 156 having threads 158 is secured in a threaded hole 160 of arm 74 (FIG. 3). An arrow, line or other indicator (not shown) is provided on post 156 to create a visual reference for selecting the desired position of cap 130 by aligning the proper one of quadrants 148, 150, 152 and 154 with post 156.

Depth control 52 further includes a stop ring 170 secured on shaft 38. In a preferred structure for stop ring 170 (FIG. 3), a sleeve 172 slidable on shaft 38 is provided with a trigger button 174 having a hole 176. In known manner, a curved spring 178 is secured with trigger button 174 via a pin 180. Thus, an axial opening 182 in sleeve 172 can be offset slightly from hole 176 in button 174, to provide a wedging engagement between stop ring 170 and shaft 38. By depressing trigger button 174, axial opening 182 and hole 176 are aligned, allowing shaft 38 to slide therethrough. In this manner, stop ring 170 can be adjusted along shaft 38 and secured on shaft 38 at a desired position.

During a bone milling procedure, a patella bone is placed between upper jaw assembly 26 and lower jaw assembly 28, and is clamped there between by rotating driver 42 to move jaw assemblies 26 and 28 toward each other until the patella is clamped firmly. A grater (not shown) is attached to shaft 38, with shaft 38 extended through guide bushing 54. Guide tower 50 is attached to upper jaw assembly 26 by engaging post 60 of upper jaw assembly 26 with fork 56 of guide tower 50. Screw 62 is inserted through post 60, with threads 66 thereof secured and tightened in post 60.

The height of faces 114, 116, 118 and 120 between floors 104, 106, 108 and 110, respectively, and top end 90 are selected to provide a zero penetration depth, and common required milling depths for standard patellar implants used. In an advantageous arrangement, the shallowest of notches 94, 96, 98 and 100, as shown notch 94, is provided as a zero depth notch. The remaining notches 96, 98 and 100 are provided at common milling depths deeper than the zero notch 94, for example depths of 7, 8 or 9 millimeters below floor 104 of notch 94. To adjust milling clamp 10 to control advancement of tool 18 to the desired milling depth, a zero adjustment in first made. Cap 130 is rotated on guide bushing 54 until indexing key 140 is aligned with the shallowest notch, notch 94 as shown. Cap 130 is lowered until bottom surface 142 of indexing key 140 is positioned against floor 104 of notch 94. Abutment surface 146 of cap 130 is then at the zero position. Adjustment is completed by advancing milling tool 18 until the grater (not shown) is positioned against the patella bone, and stop ring 170 is slid downwardly on shaft 38 to abut abutment surface 146.

To adjust depth control 52 to allow the desired milling depth, from the zero adjustment, shaft 38 is retracted slightly, without moving stop ring 170 relative to the position thereof on shaft 38. Cap 130 lifted and rotated as necessary to position indexing key 140 in the required one of notches 96, 98 and 100 corresponding to the desired milling depth. By doing so, abutment surface 140 is lowered relative to the zero position established earlier, and the distance of separation is equal to the difference in height of the one of faces 116, 118 and 120 for the one of notches 96, 98 and 100 selected and the height of face 114 for zero notch 94.

As the grater is again brought against the surface of the patellar bone before milling begins, stop ring 170 is separated from abutment surface 146 by the selected milling depth or penetration. As milling commences, shaft 38 slides in guide bushing 54 and the grater (not shown) slides in grater guide 32 downwardly until stop ring 170 abuts abutment surface 146. Further advancement of shaft 38 toward lower jaw assembly 28 is thereby prevented.

As can be understood from the aforedescribed procedure, the difference between the height of face 114 and the height of face 116, 118 or 120 for the selected notch 96, 98 or 100 determines the axial distance which shaft 38 can be advanced, and thereby determines the depth of the milling process in the patella bone clamped between upper jaw assembly 26 and lower jaw assembly 28. By zeroing the depth control as described, the depth to which milling occurs is the same regardless of the original thickness of the patella bone being milled. Thus, a predetermined precise depth can be achieved, as necessary, for the patellar implant being used.

Adjustment of the depth control is easily performed by lifting and rotating cap 130 relative to guide bushing 54. After indexing key 140 is properly positioned in the selected one of notches 94, 96, 98 and 100, with bottom surface 142 of key 140 positioned on the selected one of floors 104, 106, 108 and 110 and inner wall 144 of key 140 positioned along the selected one of faces 114, 116, 118 and 120, cap 130 cannot be accidentally rotated and displaced, without raising cap 130 relative to guide bushing 54 and rotating cap 130 through a quarter turn. Thus, once positioned, depth control 52 stays firmly in place to provide precise, accurate milling depth control.

Those skilled in the art will understand readily that milling tool 18 can comprise different size and types of graters, or other devices, such as, for example, a drill; and guide 32 can comprise a drill guide for accurately positioning anchor holes to receive anchor pins of an implant. Jaw assemblies 26 and 28 of clamping assembly 14 can be changed with modular inserts to receive different size patellae, or to perform cementing or other clamping procedures. Milling clamp 10 is lightweight and versatile.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A patellar milling clamp for guiding a milling tool during a patella milling procedure, the milling tool having a shaft for driving a grater, said clamp comprising:

a first jaw and a second jaw associatively connected to clamp a patella therebetween;

a grater guide secured relative to said first jaw;

a shaft guide secured relative to said first jaw;

said shaft guide having a top with a plurality of fixed elevations, and a cap adapted for engaging a selected one of said elevations to establish a variable height abutment surface; and a stop associated with the shaft for engaging said abutment surface and terminating movement of said shaft toward said second jaw.

2. The milling clamp of claim 1, said shaft guide including a cylindrical bushing having an end surface and a plurality of perimeter notches, each notch having a floor spaced a different distance from said end surface.

3. The milling clamp of claim 2, said cap having an indexing key selectively positioned on one of said floors of said notches.

4. The milling clamp of claim 3, said first jaw and said second jaw connected to crossed handles.

5. The milling clamp of claim 1, said shaft guide being detachable affixed to said first jaw.

6. The milling clamp of claim 5, said shaft guide including a cylindrical bushing having an end surface and a plurality of perimeter notches, each notch having a floor spaced a different distance from said end surface.

7. The milling clamp of claim 6, said cap having an indexing key selectively positioned on one of said floors of said notches.

8. A surgical instrument for clamping a bone and guiding a milling tool against the bone, said instrument comprising:

an upper handle assembly and a lower handle assembly crossed with each other;

an upper jaw assembly connected to said lower handle assembly;

a lower jaw assembly connected to said upper handle assembly; and a guide tower detachabably affixed to said upper jaw assembly, said guide tower including a guide bushing having a plurality of fixed elevations and a cap selectively positioned for engaging a selected one of said plurality of fixed elevations.

9. The surgical instrument of claim 8, said guide tower including a leg detachably secured to said upper jaw assembly and an arm connected between said leg and said guide bushing.

10. The surgical instrument of claim 9, including a screw secured through said leg into said upper jaw assembly.

11. The surgical instrument of claim 9, said guide bushing having an end surface and a plurality of perimeter notches, each notch having a floor spaced a different distance from said end surface.

12. The surgical instrument of claim 11, each notch having a flattened face from said end surface to said floor of said notch.

13. The surgical instrument of claim 12, said cap including an indexing key having a wall and a bottom surface for engaging a selected one of said notches.

14. The surgical instrument of claim 12, said guide bushing having four said notches.

15. The surgical instrument of claim 14, said upper jaw assembly including a post and said leg including a fork slidable over said post.

16. The surgical instrument of claim 14, said upper jaw assembly including a grater guide extending outwardly from an end thereof, said grater guide being in axial alignment with and spaced from said bushing.

17. A bone milling depth control for a surgical instrument having top and bottom jaws for clamping a bone, and a milling tool guide assembly for positioning a milling tool relative to the bone during a milling procedure, said milling tool being driven by a shaft, said depth control comprising:

a bushing spaced from said milling tool guide and in alignment therewith, said bushing adapted for guiding the shaft for axial movement;

said bushing having an end surface and a plurality of fixed elevations at different spaced distances from said end surface;

a cap slidable over said bushing for selectively engaging a selected one of said fixed elevations; and a ring adjustably fixed to the shaft for abutting said cap to restrict axial advancement of the shaft toward a bone clamped in the jaws.

18. The depth control of claim 17, said plurality of fixed elevations comprising perimeter notches, each notch having a floor spaced a different distance from said end surface.

19. The depth control of claim 18, each said notch having a flattened face from said end surface to said floor of said notch.

20. The depth control of claim 19, said cap including an indexing key having a wall and a bottom surface for engaging a selected one of said notches.

21. The depth control of claim 20, said guide bushing having four said notches.

* * * * *

UNITED STATES PATENT AND TRADEMARK OFFICE
CERTIFICATE OF CORRECTION

PATENT NO.   : 6,866,667 B2
DATED        : March 15, 2005
INVENTOR(S)  : Wood et al.

It is certified that error appears in the above-identified patent and that said Letters Patent is hereby corrected as shown below:

Title page,
Item [56], References Cited, U.S. PATENT DOCUMENTS, after "2,291,413 A", please delete "9/1942", and substitute therefore -- 7/1942 --; and
OTHER PUBLICATIONS,
"Dow Corning Wright" reference, please delete "We-re", and substitute therefore -- We're --.

Column 5,
Line 67, please delete "upperjaw", and substitute therefore -- upper jaw --.

Signed and Sealed this

Thirteenth Day of December, 2005

JON W. DUDAS
*Director of the United States Patent and Trademark Office*